United States Patent [19]
He

[11] Patent Number: 5,530,572
[45] Date of Patent: Jun. 25, 1996

[54] ELECTRONIC LIGHT CONTROL VISOR WITH TWO MUTUALLY PERPENDICULAR UNIDIMENSIONAL PHOTODETECTOR ARRAYS

[76] Inventor: Fan He, University of Miami, Physics Dept., Coral Gables, Fla. 33124

[21] Appl. No.: 323,181

[22] Filed: Oct. 14, 1994

[30] Foreign Application Priority Data

Mar. 8, 1994 [CN] China ................... 94206732 0

[51] Int. Cl.[6] ............ G02F 1/1335; G01J 1/20; G01J 1/32
[52] U.S. Cl. ............ 359/72; 250/201.1; 250/205
[58] Field of Search ................... 359/36, 54, 72; 250/201.1, 205, 206.2; 351/44

[56] References Cited

PUBLICATIONS

Custom Liquid Crystal sales information (4 pages), UCE, Inc., Nov. 15, 1993.

*Primary Examiner*—Anita Pellman Gross
*Assistant Examiner*—Walter J. Malinowski

[57] ABSTRACT

An electronically controlled visor that includes a panel composed of a number of liquid crystal pixels that act as shutters to attenuate offending light sources. The pixels are driven by an electronic control unit that in turn is driven by light sensor assemblies that detect the angle of incidence of the offending radiation. A correlation exists between the elements of the light sensor that are activated and the pixels that end up being energized, changing their opacity, as a result of detecting the offending light source so that the latter can be attenuated. A bias adjustment control circuit adjusts the level of light that is to be considered offending (damaging or distracting to a user). Sections of the panel comprising several pixels can be activated together, or in non-contiguous patterns in order to optimize the effectiveness of the attenuation with a minimum of peripheral unneeded attenuation of neighboring pixels.

5 Claims, 6 Drawing Sheets

Horizontal Sensor Array

Vertical Sensor Array

ELECTRONIC LIGHT CONTROL VISOR WITH TWO MUTUALLY PERPENDICULAR UNIDIMENSIONAL PHOTODETECTOR ARRAYS

BACKGROUND OF THE INVENTION

1. Field of the Invention

The present invention relates to visors used to block disturbing light sources affecting an operator of a vehicle or other equipment, and more particularly, to such visors with transparency coefficients that are electronically controlled.

2. Description of the Related Art

Many different designs of visors have been designed in the past. However, to the best of applicant's knowledge, all of these designs have been mechanical and use opaque, or semi-opaque bodies that are interposed between the light source and the user. There has been no electronically controlled visor wherein only a portion of the visor is obscured keeping the rest of the area transparent for the user's benefit. None of the designs known to applicant provide for a mechanism for blocking only the offending source of light nor do they provide for an adjustment of what constitutes an offending light source.

SUMMARY OF THE INVENTION

It is one of the main objects of the present invention to provide a visor that selectively and closely tracks the areas of a visor panel where attenuation of a light source is desired without affecting the transparency of surrounding areas.

It is another object of this invention to provide a visor that is electronically controlled and that does not require the use of movable parts.

It is still another object of the present invention to provide a visor that can be adjusted to different levels of light.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 1:
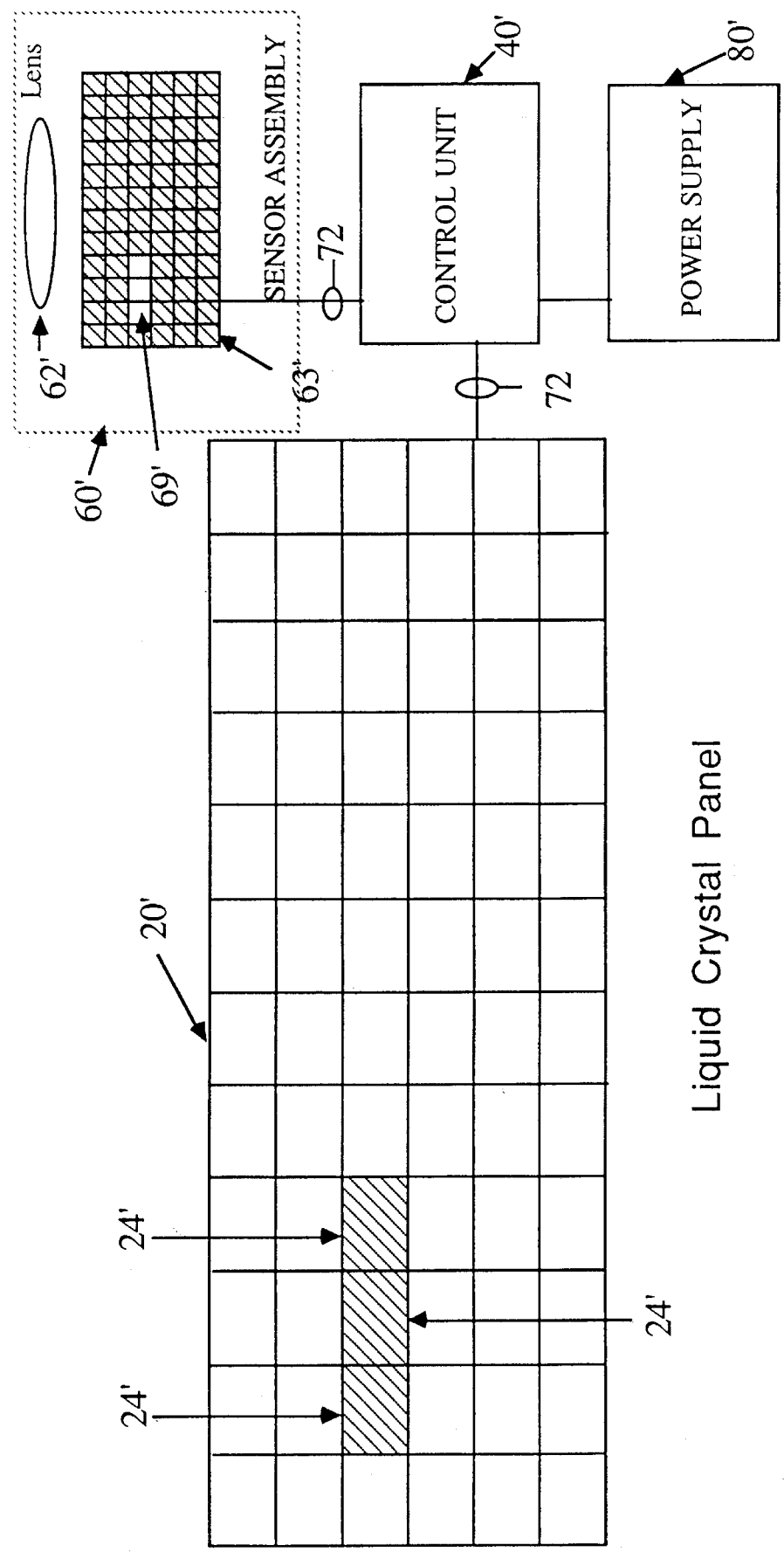
FIG. 1 represents a schematic diagram of the electronic visor incorporating the subject matter claimed in this application. A two-dimensional sensor array shows three photoelements activated through a lens causing three sections, of six pixels each, of the visor panel to be activated.

Referring now to the drawings, and in particular to FIG. 1, where the present invention is generally referred to with numeral 10, it can be observed that it basically includes liquid crystal panel 20, control unit 40, sensor assembly 60 and power supply 80. Panel 20 is positioned between a user and the sources of light being monitored. In a typical situation, a user is behind the wheel of a vehicle monitoring light sources and the reflection of the light from the sources on objects and people. Depending on what the user observes, he or she takes actions on the operation of the equipment. Some of these light sources (the sun, beams of light from approaching vehicles, etc.) may become offensive or disturbing to the user. Blocking or attenuating these offending light sources then becomes not only desirable but necessary for the safe operation of the equipment or vehicle. Section 24 in FIG. 1 represents a group of six pixels grouped together to block or attenuate the offending light source.

In FIG. 1, sensor assembly 60 includes lens member 62 and two-dimensional photosensitive array 63 (consisting of 12×6 units for a total of 72 photo-diodes). Lens member 62 is designed so that the offending light source affects three photo-diodes, in this embodiment, and through control unit 40, causes three sections 24 to be activated. Each section 24 has six pixels 22 that are hardwired together.

Figure 2:
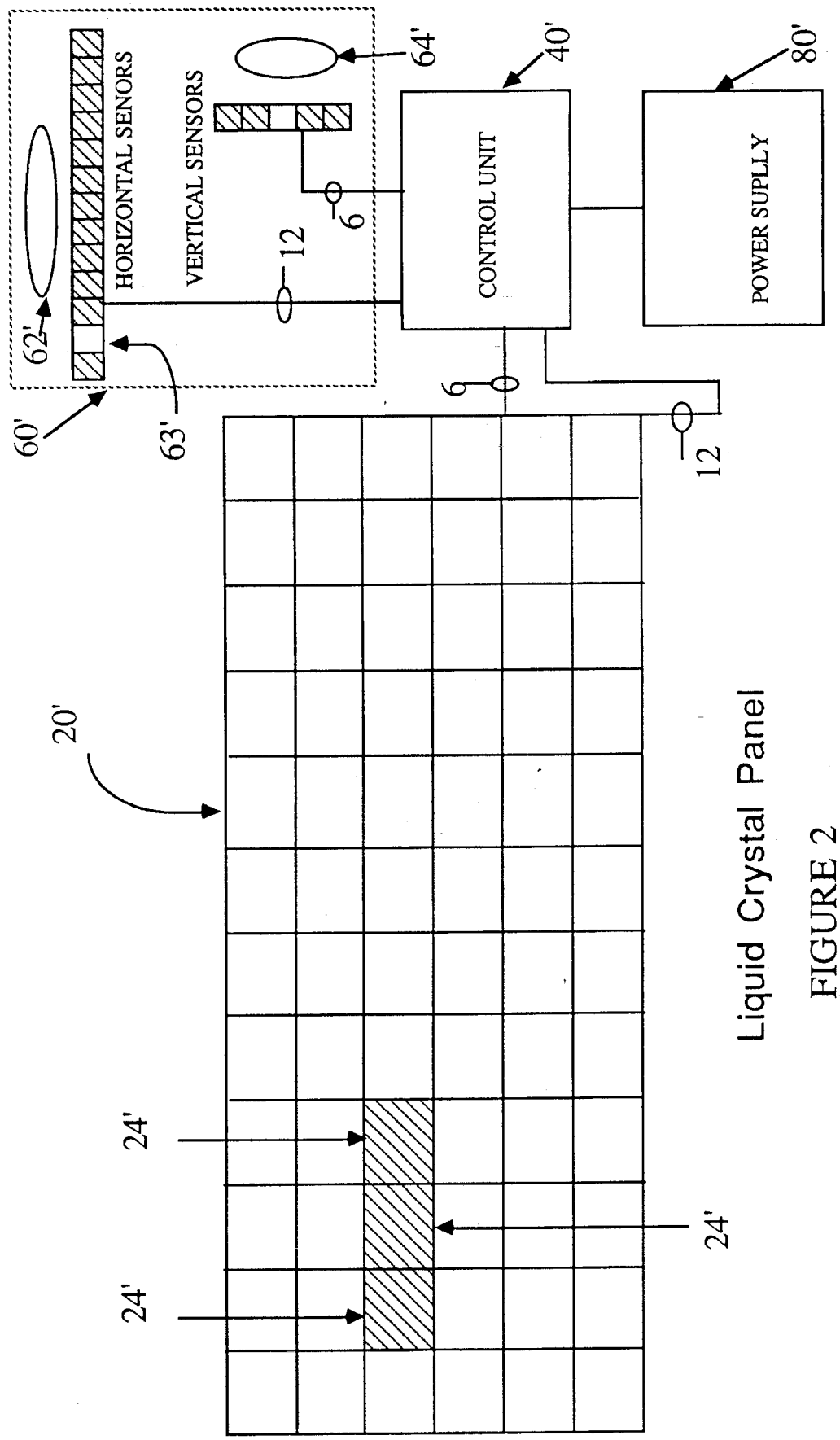
FIG. 2 shows a schematic diagram for an alternate embodiment incorporating two longitudinally extending sensor assemblies, instead of the two-dimensional array shown is FIG. 1, that are perpendicularly disposed with respect to each other.

In FIG. 2, sensor assembly 60' includes one-dimensional elongated horizontal sensor member 63' and elongated vertical one-dimensional sensor member 65' with corresponding lens members 62' and 64'. Elongated horizontal sensor member 63' is perpendicularly disposed with respect to elongated vertical sensor member 65'. With twelve and six outputs from members 63' and 65', respectively, the horizontal and vertical axes can provide the location on panel 20' corresponding to sections 24' of pixels 22' that need to be activated by control unit 40'. Power supply 80' provides the necessary electrical power to operate control unit 40' and panel 20'.

Figure 3:
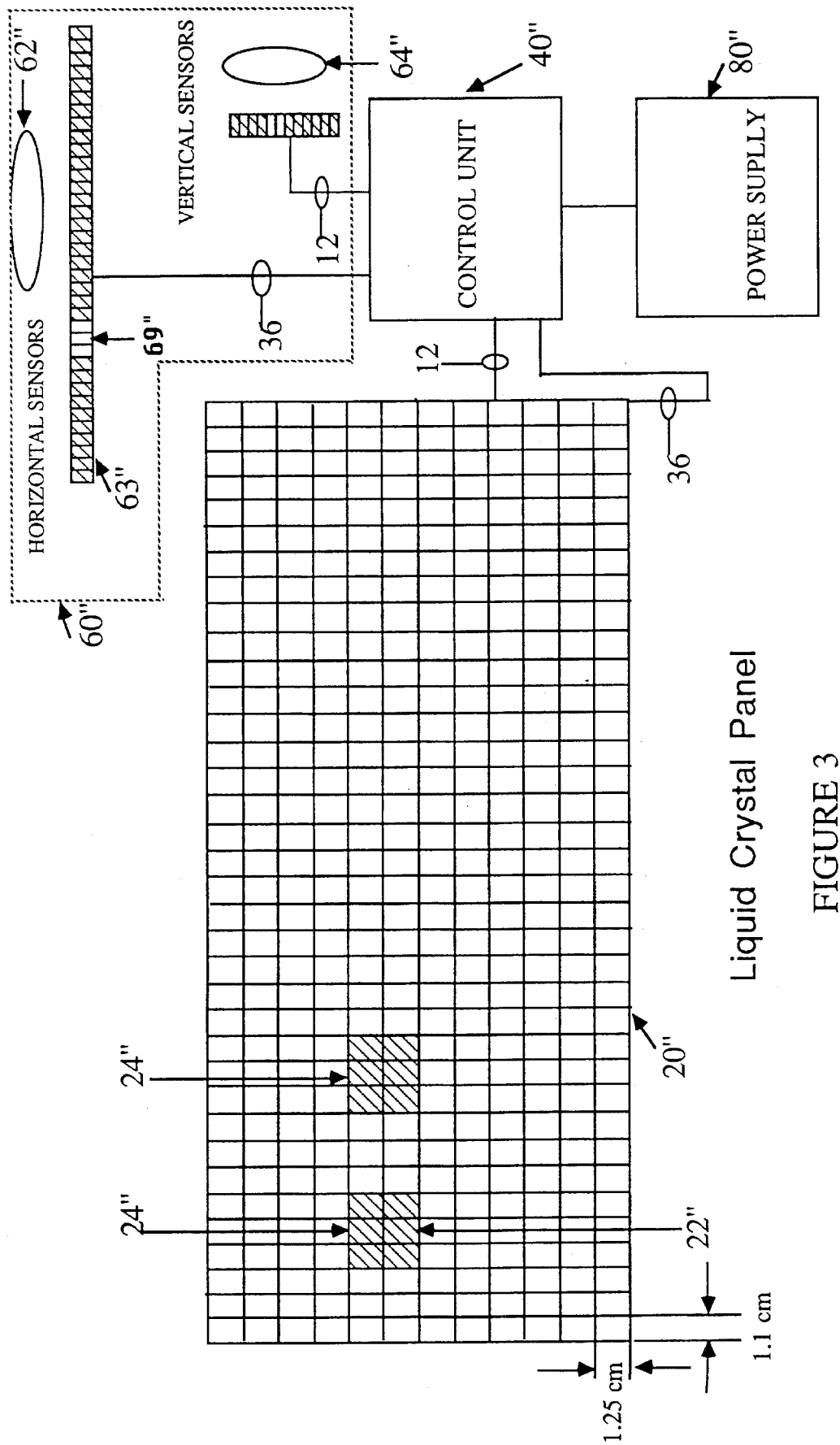
FIG. 3 represents the same device as in the previous figure, except that the sections, of six pixels each, that are activated are not contiguous.
Figure 4:
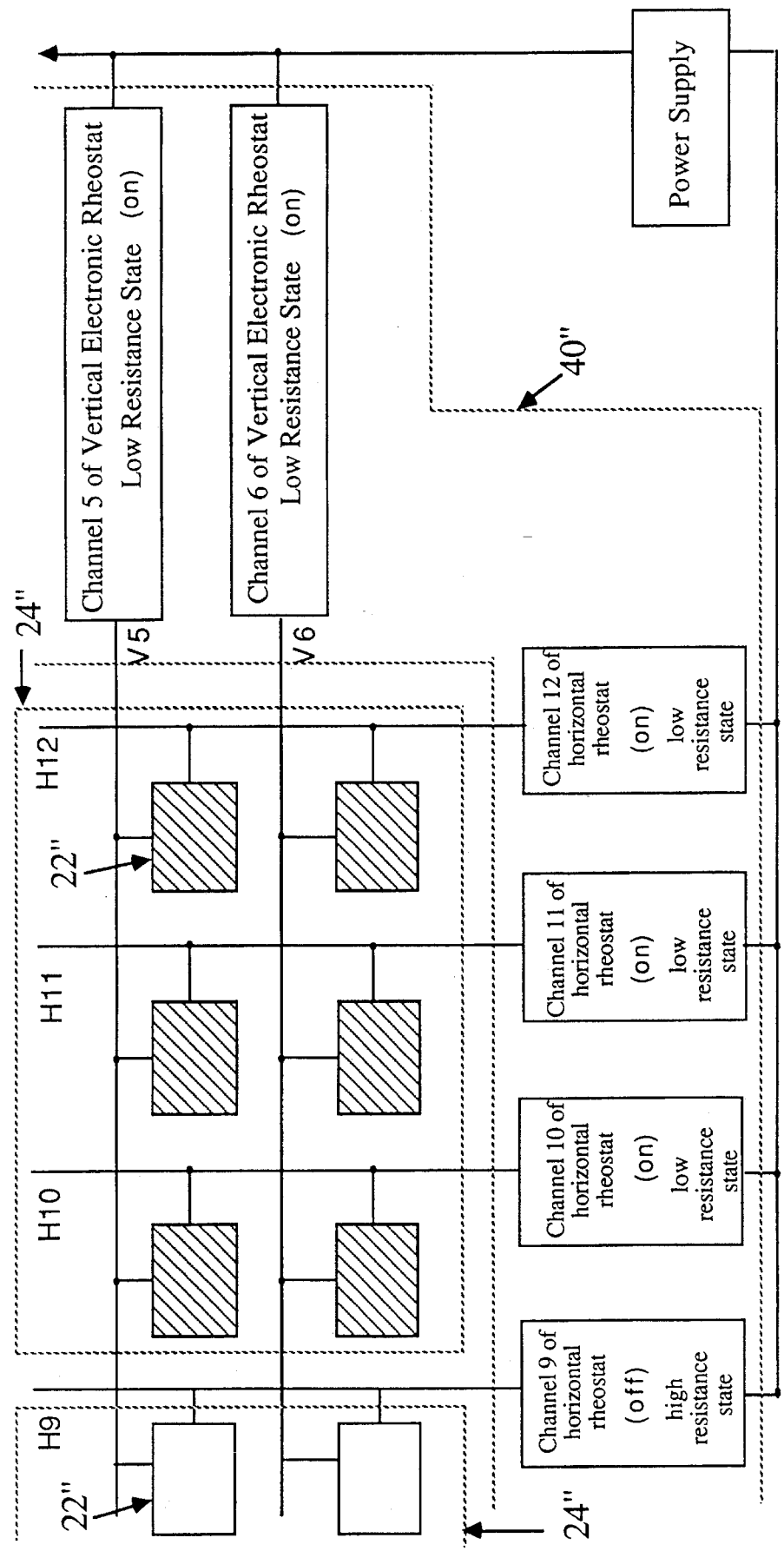
FIG. 4 is a partial representation of the electronic unit controlling the liquid crystal pixels.

In FIG. 3, circuit control unit 40" is designed so that non-contiguous sections 24" are activated. The dimensions of these sections are such that the distance between the respective centers corresponds, approximately, to the separation between the pupils in the average human being, or about 6 cm. In the preferred embodiment, the height of section 24" (24 and 24' also) is 2.50 cm. and its width is 3.3 cm.

Panels 20; 20' and 20" include a number of identical liquid crystal pixels 22; 22' and 22". These pixels are shutters with their transparency being controlled by an input voltage signal. Depending on the intensity of the offending light source on sensor assemblies 60; 60' and 60", the coefficient of transparency in the corresponding activated pixels 22; 22' and 22" will then be reduced (or opacity in are used). Liquid crystal pixels 22; 22' and 22" can be implemented, among others, with liquid crystal shutter type CID manufactured by UCE, Inc., 35 Rockland Rd., Norwalk, Conn. 06854. A predetermined number of pixels are always turned on together and they constitute sections 24; 24' and 24", as best seen in FIGS. 1 through 4. Sections 24; 24' and 24" include six pixels 22; 22' and 22", respectively, having a rectangular shape with 1.25 cm. in height and 1.1 cm. in width, in the preferred embodiment. Panels 20; 20' and 20" include twelve rows and thirty six columns for each of these embodiments.

Control unit 40, in FIG. 1, includes the necessary circuit to provide the one to one (photosensitive element 69 to sections 24) corresponding activation of sections 24. Control unit 40 includes multi-channel electronic rheostat circuit 42 which can be implemented with an integrated circuit manufactured by Analog Devices under part No. MUX 24. Basically, each analog output from photo-diode array 63 is connected to an input in multi-channel electronic rheostat circuit includes in control unit 40. This electronic rheostat circuit will provide an amplified output to drive a corresponding section 24 having six pixels 22. Pixels 22 will correlate in position with the photo-diodes 69 in array 63 that were activated by the offending light source. The higher the intensity of the offending light source, the higher the voltage transmitted to pixel 22, the higher the opacity (lower transparency), thereby increasing the attenuation of the offending light.

Control unit 40' in FIG. 2 operates similar to the one described above, except that it receives less outputs from sensor assembly 60'. The outputs received are the ones necessary to locate the position in panel 20' for the pixels 22' that will be used to block or attenuate the offending light source.

Control unit 40" in FIG. 3 works like control unit 40' except that the circuit is designed to activate section 24" that are not contiguous in order to effectively attenuate the offending light source with a minimum of opacity in the surrounding area.

Figure 5:
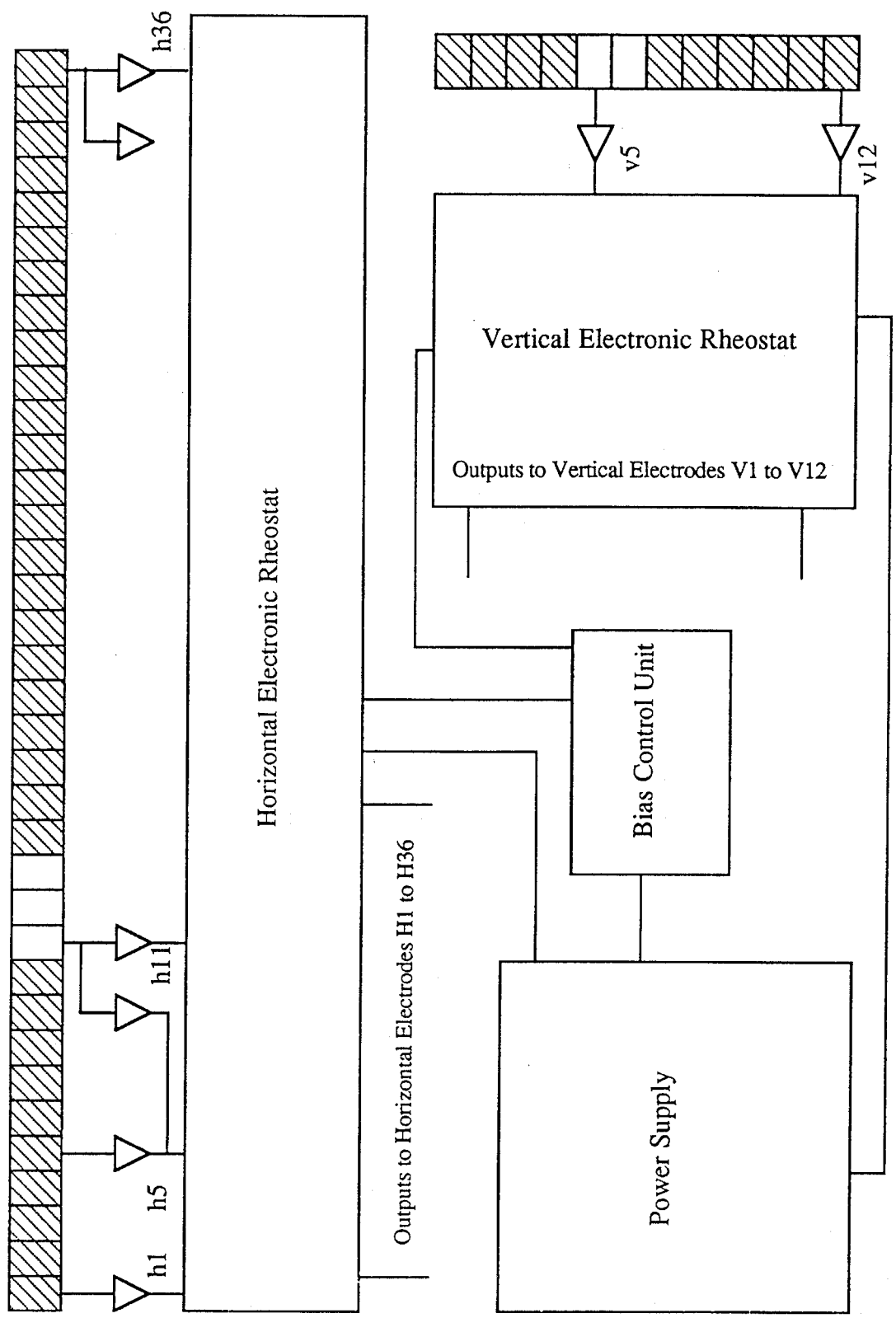
FIG. 5 is a schematic representation of the alternate embodiment shown in FIG. 3 wherein the elongated horizontal sensor assembly has three photo-diodes activated and the elongated vertical sensor assembly has two photo-diodes activated.
Figure 6B:
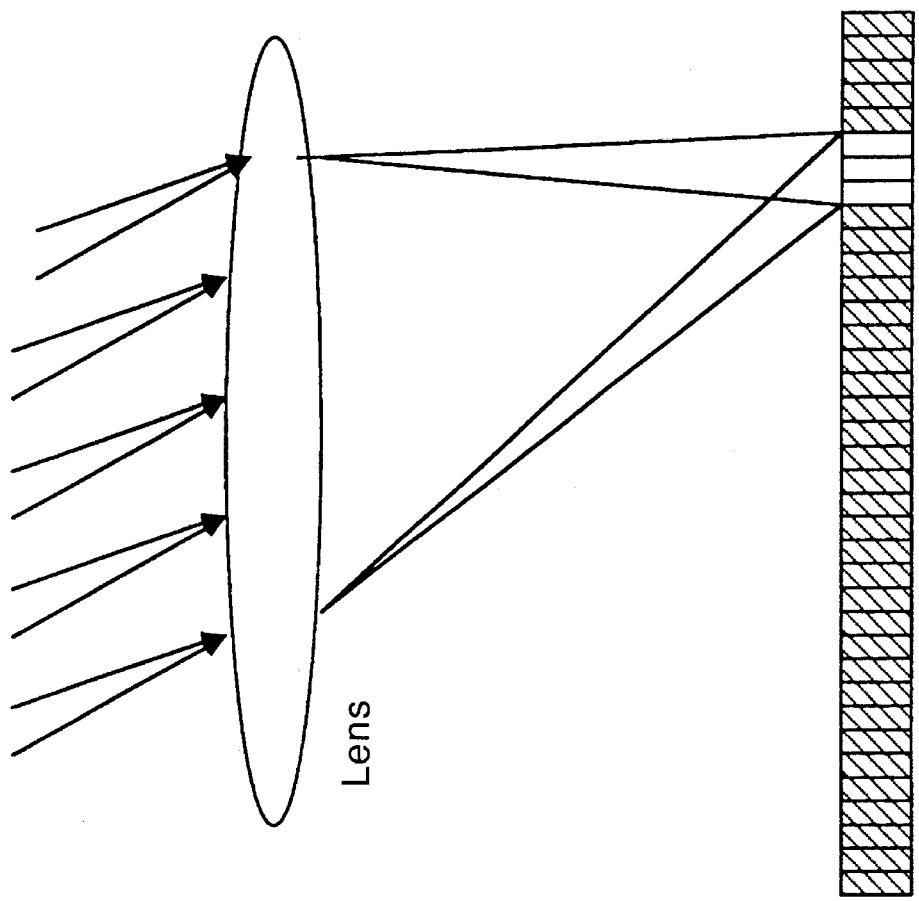
FIG. 6B shows the characteristic of the lens used in the preferred embodiment for the horizontal sensor array.
Figure 6A:
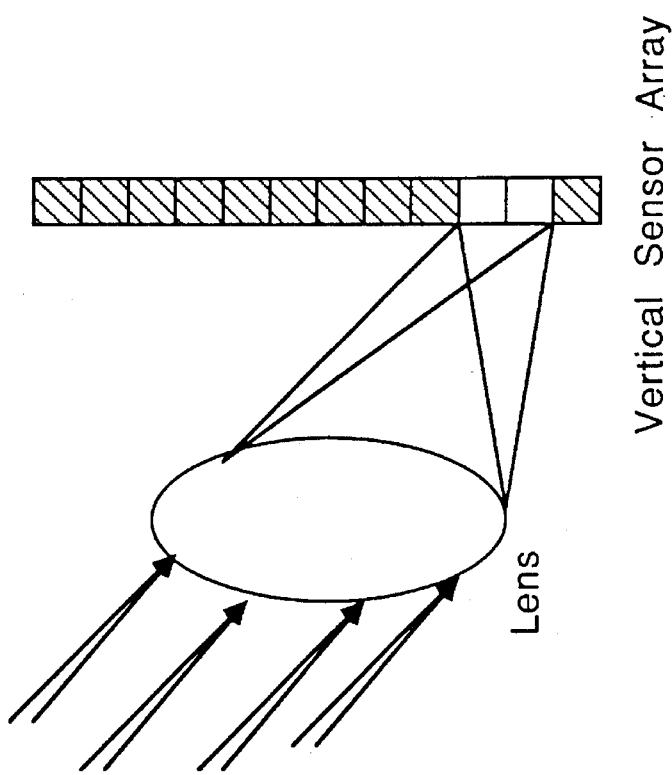
FIG. 6A shows the characteristics of the lens used in the preferred embodiment for the vertical sensor array.

To establish a light reference point bias, control unit 48" is adjusted, as best seen in FIG. 5. Bias control unit 48" can be implemented with gain amplifier 47" and photodiode 46". In this manner, only the offending light source will cause the opacity of the critical pixels to increase. For example, if panel 20" is adjusted at night, only the beams from approaching vehicles will be considered offending light sources. Without unit 48" the same circuitry would cause the entire panel to be opaque in broad daylight. Circuits 68; 68'; and 68" are included in control units 40; 40' and 40".

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An electronically controlled visor for attenuating offending light sources, comprising:

A. light sensor means for detecting said offending light source including a plurality of first outputs, and said light sensor means includes a plurality of light sensitive elements disposed on a plane and lens means adapted to activate a predetermined number of said light sensitive elements in response to the position of said offending light source, wherein said light sensitive elements are longitudinally disposed in two uni-dimensional arrays substantially perpendicular to each other and in cooperative correlation with the position of said liquid crystal pixel means to attenuate said offending light sources;

B. control circuit means having a plurality of first inputs connected to said plurality of first outputs of said sensor means and said control circuit means includes a plurality of second outputs;

C. panel means having a corresponding plurality of liquid crystal pixel means connected to said plurality of second outputs so that when said light sensitive elements are activated, cooperatively corresponding liquid crystal pixel means are also activated through said control circuit means, thereby attenuating said offending light sources; and D. bias control means for adjusting the sensitivity of said control circuit means so that a light reference can be provided to automatically adjust for ambient light levels.

2. The visor set forth in claim 1 wherein said control circuit unit means includes circuit means for producing outputs that activate said liquid crystal pixel means in groups.

3. The visor set forth in claim 2 wherein said activated groups are non-contiguous.

4. The visor set forth in claim 3 wherein the activation consists of two groups of said liquid crystal pixel means.

5. The visor set forth in claim 4 wherein said groups are separated from the respective centers of each group a distance that approximately coincides with the separation of the pupils of a user.

\* \* \* \* \*